United States Patent [19]

Schoenwald et al.

[11] Patent Number: 4,968,718

[45] Date of Patent: Nov. 6, 1990

[54] TOPICALLY EFFECTIVE, NONSTEROIDAL DRUG FOR USE IN EXTERNAL AND INTERNAL EYE INFLAMMATIONS

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 147,974

[22] Filed: Jan. 25, 1988

[51] Int. Cl.$^5$ .............................................. A01N 37/10
[52] U.S. Cl. ..................................... 514/532; 514/570
[58] Field of Search ................................ 514/532, 570

[56] References Cited

U.S. PATENT DOCUMENTS

| 3,228,831 | 1/1966 | Nicholson | 514/568 |
| 3,991,206 | 11/1976 | Tolman et al. | 424/317 |
| 4,028,404 | 6/1977 | Bays et al. | 260/515 R |
| 4,181,736 | 1/1980 | Maillard | 424/317 |
| 4,251,543 | 2/1981 | Amano et al. | 424/317 |
| 4,599,360 | 7/1986 | Fukami et al. | 514/570 |
| 4,622,421 | 11/1986 | Terada et al. | 562/491 |

FOREIGN PATENT DOCUMENTS

| 2250400 | 5/1973 | Fed. Rep. of Germany . |
| 2814556 | 10/1978 | Fed. Rep. of Germany . |
| 2904799 | 8/1979 | Fed. Rep. of Germany . |
| 3026402 | 2/1982 | Fed. Rep. of Germany . |
| 2403325 | 5/1979 | France . |
| 2053833 | 4/1977 | Japan . |
| 2027015 | 2/1980 | United Kingdom . |

Primary Examiner—Paul J. Killos
Attorney, Agent, or Firm—Zarley, McKee, Thomte, Voorhees & Sease

[57] ABSTRACT

A nonsteroidal anti-inflammatory drug which is phenylacetic acid derivative and methods of using the same in topically controlling eye inflammations.

17 Claims, No Drawings

TOPICALLY EFFECTIVE, NONSTEROIDAL DRUG FOR USE IN EXTERNAL AND INTERNAL EYE INFLAMMATIONS

BACKGROUND OF THE INVENTION

This invention relates to a method and compositions useful in treating both internal and external eye inflammations. Specifically, this invention relates to methods and compositions which use certain nonsteroidal anti-inflammatory drugs to control internal and external eye inflammation.

For over a decade nonsteroidal anti-inflammatory drugs have been tested for their ability to suppress corneal inflammations. Indomethacin, fenoprofen, oxyphenbutazone, suprofen, and flurbiprofen were found to be effective in the laboratory and in the clinic for treating postoperative corneal inflammations. When compared to the commercially available topical corticosteroids, the nonsteroidal anti-inflammatory drugs are not as effective in treating corneal inflammations. Also, the currently available nonsteroidal anti-inflammatory drugs appear to have very little usefulness in clinically treating inflammations of the anterior chamber.

The nonsteroidal anti-inflammatory drugs were designed for systemic use and not for topical application to the eye. However, the requirements for optimal pharmacokinetics in the eye are quite different when compared to the systemic route of administration. An additional limitation to use of nonsteroids for ophthalmic use is their intrinsic pharmacological activity, which has been shown to be lower than the corticosteroids. These factors make it important to design molecules specially for the eye if topical application of nonsteroids is to be successful.

An object of this invention is to improve corneal penetration and most importantly, to improve distribution to and retention within, the iris/ciliary body tissue of nonsteroid drugs for inflammation treatment. Topical therapy using nonsteroidal anti-inflammatory drugs for corneal and anterior chamber inflammations would be very advantageous compared to the use of the corticosteroids. Steroids are responsible for various unwanted side effects, such as, an increase in intraocular pressure, delayed wound healing, cataract formation and corneal perforation.

As earlier stated, most inflammations of the eye are currently treated by other steroids which penetrate the eye and work effectively, but cause undesirable side effects. The undesirable side effects referred to earlier are exemplified by increased intraocular pressure, delayed wound healing, cataract formation and corneal perforations. On the other hand, if steroids are replaced with nonsteroidal anti-inflammatory drugs which do not penetrate the eye in therapeutic concentrations, they are generally effective only for external inflammations and thus have limited therapeutic application, i.e. pre-surgery. It thus can be seen that a continuing need exists for a drug which would both penetrate and be effective for not only external, but internal eye inflammations, and at the same time be free of systemic side effects.

The primary objective of the present invention is then to provide a nonsteroidal anti-inflammatory drug which will effectively penetrate the eye in therapeutic concentrations, which is effective for both internal and external inflammations, and which does not cause the typical systemic side effects of steroidal anti-inflammatory drugs.

SUMMARY OF THE INVENTION

Certain phenylacetic acid derivatives have been found to be effective nonsteroidal anti-inflammation drugs for ophthalmic use. They are effective both for external inflammations and internal inflammations and do not cause systemic side effects, as do steroidal drugs. The invention discloses certain compounds of the type below described, and ophthalmically acceptable salt forms thereof, and the method of using the same for topically treating inflammations of the eye, and pharmaceutical compositions which contain these active anti-inflammatory nonsteroidal compounds.

DETAILED DESCRIPTION OF THE INVENTION

The compounds which are effective for use in this invention have the formula:

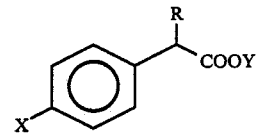

wherein R=hydrogen or $C_1$ to $C_5$ alkyl, X=mono-, di-, tri- and tetrahydroxy substituted $C_2$ to $C_{10}$ alkyls, and y=hydrogen, $C_1$ to $C_5$ straight or branched chain alkyl, particularly pivalyl. Included also are ophthalmically acceptable salt forms of each compound. These compounds may exist in several steroisomeric forms. All of the steroisomeric forms are therapeutically active. Thus, they are all intended to be within the scope of this invention, both (R, S) and racemic modifications thereof.

It is preferred that R=hydrogen or methyl and that X= monohydroxy substituted $C_2$ and that y=hydrogen or pivalyl.

It is believed that the active compound is where "y" equals hydrogen, but prodrugs may be metabolized to this form and be active. Thus, prodrugs which are designed to cross the cornea rapidly may be desirable, such as the pivalyl.

The ophthalmically active compounds may be incorporated into various ophthalmic formulations for delivery to the eye. For example, the compounds may be combined with ophthalmologically acceptable preservatives, surfactants, viscosity enhancers, buffers, sodium chloride and water to form an aqueous ophthalmic suspension. In order to form sterile ophthalmic ointment formulations, the active ingredient is combined with a preservative in an appropriate vehicle, such as mineral oil, liquid lanolin, or white petrolatum. Sterile ophthalmic gel formulations may be prepared by suspending the active nonsteroidal drugs of this invention in a hydrophilic base prepared from a combination of carbopol -940 (a carobxy vinyl polymer available from the B. F. Goodrich Company) according to published formulations for analogous ophthalmic preparations. Preservatives and tonicity agents can also be incorporated.

The specific type of formulation selected will depend on various factors, such as the type of ophthalmic inflammation being treated and dosage frequency. Ophthalmic solutions or suspensions suitable for easy eye drop administration, ointments and gels are the preferred dosage forms.

The active, nonsteroidal compounds of this invention will normally be contained in these formulations in an amount of from about 0.05% by weight to about 5.0% by weight, preferably from about 0.5% by weight to about 3.0% by weight. Thus, for topical presentation these formulations may be delivered in modest excess to the surface of the eye from 1–6 times per day depending upon the discretion of the clinician.

As heretofore mentioned, the compounds per se of the invention may be used or ophthalmically acceptable salt forms thereof. The ophthalmologically acceptable salts of the compounds of this invention include those formed from inorganic bases such as Group I hydroxides, like sodium hydroxide, and those formed from organic bases such as amines, etc.

Suitable ophthalmically acceptable carriers are generally known and of course must be non-eye-irritating, non-toxic, and allow for safe, easy eye administration topically. Generally for this invention aqueous-base systems wherein the carrier includes a buffer system to provide eye safe pH, a viscolyzer to provide suitable viscosity for eye comfort, an antibacterial agent, and a chemical preservative are adequate. The ophthalmically acceptable buffer should provide a composition having a pH within the range of about 5.5 to about 7.8, preferably from about 6.8 to about 7.4. Suitable ophthalmically acceptable buffers can be selected from the water soluble salt forms of citrate, borate, phosphate, corbonate, and acetate.

The viscolyzer suitable for use in this invention should provide the composition with a viscosity within the range of from about 4 centipoises to about 100 centipoises, preferably from about 5 centipoises to about 35 centipoises. Suitable viscolyzers can be selected from the group consisting of hydroxyethylcellulose, hydroxypropyl methylcellulose, methylcellulose and a polyacrylamide sold under the trade name GELAMIDE 250 by American Cyanamide.

In addition, the ophthalmic composition ideally will include antibacterials to provide safety and efficacy for storage stability. The amount of antibacterial can be within the range of from about 0.004% to about 0.5% by weight/volume of the composition. A suitable antibacterial would include, for example, from about 0.004% to about 0.02% by weight/volume of benzalkonium chloride, from about 0.25% to about 0.5% of chlorobutanol, about 0.1% of thimerosal, about 0.05% methylparaben, about 0.01% propylparaben, and sodium chloride in an amount sufficient to make an isotonic solution.

Finally, chemical preservatives may also be used, for example sodium thiosulfate at about a 0.3% level and ethylenediaminetetraacetic acid at about 0.05%.

It goes without saying that the precise ophthalmic carrier must be selected to provide pharmaceutical elegance, to provide eye comfort and to allow for effective topical administration. Formulation of such is well within the skill of the ordinary artisan who prepares ophthalmic carrier compositions.

The compounds used as the anti-inflammatories of this invention have features which enhance the aqueous solubility of the anti-inflammatory drug while retaining sufficient lipid solubility to promote intraocular penetration. They also will maintain the pharmacophore necessary to exhibit anti-inflammatory activity. The compounds thus take into account both solubility for sufficient ocular penetration and anti-inflammatory activity, and balance these in unique compounds duly suited for the unique penetration and distribution processes for drugs in the eye.

The following examples serve to further illustrate but not limit the compounds, compositions and method of the present invention. A rabbit cornea model was used in the tests shown in the examples because, as those of ordinary skill in the art know, rabbit cornea testing has been mostly correlated with test results for the human eye, R.D. Schoenwald et al, *Biopharm. Drug Dispos.*, 3, 231 (1982).

EXAMPLES

Excised rabbit corneas were carefully mounted between two halves of a plastic cylinder. Various concentrations of Ibuprofen as a comparative model:

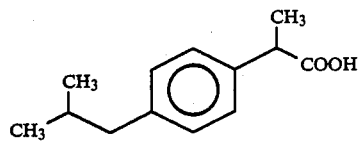

or the compound of the present invention wherein R and Y= hydrogen and X=hydroxyethoxy were placed on the epithelial side initially and drug appearing on the endothelial side was measured over time.

The slope from the quantity of drug crossing the excised cornea over time was used to calculate the corneal permeability coefficient (cm/sec):

TABLE I

| Initial Cell Conc. (mcg/mL) | Permeability Coefficient ($\times 10^{-6}$ cm/sec) | |
| --- | --- | --- |
| | Ibuprofen | Invention |
| 500 | 21.6 | — |
| 250 | 23.9 | 6.42 |
| 150 | 21.2 | 6.65 |
| 60 | 22.8 | 6.53 |
| | mean = 22.4 | mean = 6.53 | pH = 7.6, temp. = 37, 95% $O_2$ 5% $CO_2$

The solubilities of the two were compared and found to be as follows:
Ibuprofen: 75 mcg.m/L (in dist. water, pH=5.5)
(Invention): 5000 mcg/mL (in dist. water, pH=5.0)
When the maximum penetration rate (MPR) is calculated: MPR= (SOL) (Perm. Coeff.), Ibuprofen equals 1.68 mg/cm²/sec and the invention is 32.7 mg/cm²/sec. Thus, the invention has a 19.5 fold greater corneal penetration rate.

Corneal anti-inflammatory activity was compared. The Leibowitz anti-inflammatory model was used, H.M. Leibowitz and A. Kupferman, "Anti-inflammatory effectiveness in cornea of topically administered prednisolone," *Invest. Ophthalmol.*, 13, 757 (1974) and H.M. Leibowitz and A. Kupferman, "Bioavailability and therapeutic effectiveness of topically administered corticosteroids," *Trans. Am. Acad. Ophthalmol. Otolaryngol.*, 79, 78 (1975). This method consists of first injecting tritiated thymidine intravenously into white rabbits. In approximately 2 days, the radioactive, thymidine is incorporated into polymorphonuclear leucocytes (PMN) which upon injection of clover oil into the stroma of the cornea will migrate to the site of injection. Topical treatment of nonsteroidal anti-inflammatory drugs, if effective, will suppress the migration of polymorphonuclear cells to the injection site. The reduction of radioactivity in the cornea becomes a measure of drug effectiveness to suppress the inflammation process. The results are summarized below as a percent reduction of radioactivity occurring from no drug treatment.

TABLE II

| Drug Treatment* | DPM** | % Decrease (compared to control) |
|---|---|---|
| Invention 1% Solution | 6720 (sd = 3368) | 19 |
| Prednisolone Acetate 1% Suspension | 4288 (sd = 2846) | 48 |
| No Treatment | 8255 (sd = 5956) | 0 |

*Drug treatment started at the time of clove oil injection (N = 6/treatment group); all treatment groups received 8-9 doses/day of Invention.
**Disintegrations per minute Prednisolone acetate was used as a comparative, highly effective steroidal anti-inflammatory, which like many of the other effective ones is known to produce certain undesirable side effects.

The initial results for the topical instillation of 1% of the invention show a 19% decrease in corneal inflammation following clove oil chemotaxis. These results for the invention are significantly less potent than the results observed for 1% prednisolone acetate suspension. This is not surprising in light of the superior potency of steroids, particularly prednisolone acetate, and the generally lower potency of nonsteroidal anti-inflammatory drugs. The values obtained for 1% prednisolone acetate agree with published results by Leibowitz. Ibuprofen itself is reported to be effective for post-operative corneal inflammation in patients taking 1200 Gm/day, but no reports are published to indicate its topical efficacy on corneal inflammation. The superior permeability characteristics of the compound of the present invention over Ibuprofen indicates much higher effective activity without systemic side effects.

What is claimed is:

1. A method of effectively and topically treating inflammations of the eye with nonsteroidal drugs so as to reduce unwanted systemic side effects, said method comprising:
    administering to an affected eye an inflammation reducing effective amount of a compound of the formula:

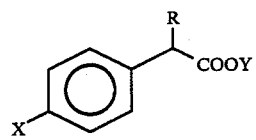

wherein R equals hydrogen or $C_1$ to $C_5$, X equals mono-, di-, tri- and hydroxy substituted $C_2$ to $C_{10}$ alkyls, and Y equals hydrogen or $C_1$ to $C_5$ straight or branched chain alkyl, or an ophthalmically effective salt form thereof.

2. The method of claim 1 wherein X equals monohydroxyethoxy.

3. The method of claim 1 wherein X equals 2,3-dihydroxypropoxy.

4. The method of claim 2 wherein R equals hydrogen.

5. The method of claim 2 wherein R equals methyl.

6. The method of claim 2 wherein the amount of said compound is from about 0.05% by weight to about 5.0% by weight.

7. The method of claim 2 wherein the amount of said compound is from about 0.5% by weight to about 3.0% by weight.

8. A nonsteroidal pharmaceutical composition for topically treating inflammation of the eye comprising an inflammation reducing effective amount of a compound of the formula:

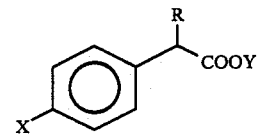

wherein R equals hydrogen or $C_1$ to $C_5$, X equals mono-, di-, tri- and tetrahydroxy substituted $C_2$ to $C_{10}$ alkyls, and Y equals hydrogen or $C_1$ to $C_5$ straight or branched chain alkyl, or an ophthalmically effective salt form thereof.

9. The composition of claim 8 wherein X equals monohydroxyethoxy.

10. The composition of claim 8 wherein X equals 2,3-dihydroxypropoxy.

11. The composition of claim 8 wherein the amount of said compound is from about 0.05% by weight to about 5.0% by weight.

12. The composition of claim 11 wherein the amount of said compound is from about 0.5% by weight to about 3.0% by weight.

13. The composition of claim 9 wherein said composition is an eye drop solution.

14. The composition of claim 9 wherein said composition is an ointment.

15. The composition of claim 9 wherein said composition is an ophthalmic gel.

16. The composition of claim 9 wherein "R" of said compound is hydrogen.

17. The composition of claim 9 wherein "R" of said compound is methyl.

* * * * *